US012569228B2

(12) United States Patent
Kamino

(10) Patent No.: US 12,569,228 B2
(45) Date of Patent: Mar. 10, 2026

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Itsuki Kamino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 146 days.

(21) Appl. No.: 18/467,926

(22) Filed: Sep. 15, 2023

(65) Prior Publication Data

US 2024/0000438 A1 Jan. 4, 2024

Related U.S. Application Data

(63) Continuation of application No. PCT/JP2022/010475, filed on Mar. 10, 2022.

(30) Foreign Application Priority Data

Mar. 22, 2021 (JP) ................................. 2021-047388

(51) Int. Cl.
*A61B 8/00* (2006.01)
(52) U.S. Cl.
CPC ............. *A61B 8/54* (2013.01); *A61B 8/4416* (2013.01); *A61B 8/463* (2013.01); *A61B 8/465* (2013.01); *A61B 8/469* (2013.01)
(58) Field of Classification Search
CPC ......... A61B 8/54; A61B 8/4416; A61B 8/463; A61B 8/465; A61B 8/469; A61B 8/467; A61B 8/14
See application file for complete search history.

(56) References Cited

U.S. PATENT DOCUMENTS

| 2002/0087080 A1* | 7/2002 | Slayton | .................... A61B 8/42 |
| | | | 600/459 |
| 2009/0024030 A1* | 1/2009 | Lachaine | ................. A61B 8/14 |
| | | | 600/437 |

(Continued)

FOREIGN PATENT DOCUMENTS

| JP | 2001-112752 A | 4/2001 |
| JP | 2015-131099 A | 7/2015 |

(Continued)

OTHER PUBLICATIONS

JP6850896 Translation (Year: 2021).*

(Continued)

*Primary Examiner* — Adil Partap S Virk
(74) *Attorney, Agent, or Firm* — Studebaker Brackett PLLC

(57) ABSTRACT

According to the present invention, in an ultrasound diagnostic apparatus and a control method for an ultrasound diagnostic apparatus, an ultrasound image generation unit is configured to generate an ultrasound image including an examination area, and an optical camera is configured to generate an optical image including a subject under examination in a state in which an ultrasound probe is in contact. A display control unit is configured to display the ultrasound image and the optical image on a monitor, and a first image memory is configured to store the ultrasound image and the optical image generated in a certain period in a past from a timing designated by a user. An image selection unit is configured to select a single frame of the ultrasound image and a single frame of the optical image from among the ultrasound images and the optical images stored in the first image memory, and a second image memory is configured to store the single frame of the ultrasound image and the single frame of the optical image in association with each other. With this, it is possible to eliminate the time and effort (Continued)

required to reselect a desired image in a case where the optical image is used instead of a body mark.

18 Claims, 5 Drawing Sheets

(56)                References Cited

U.S. PATENT DOCUMENTS

| | | | | |
|---|---|---|---|---|
| 2010/0286518 A1* | 11/2010 | Lee | ............................ | A61B 8/08 |
| | | | | 600/439 |
| 2012/0179039 A1* | 7/2012 | Pelissier | ................. | H04N 19/61 |
| | | | | 600/443 |
| 2014/0221825 A1* | 8/2014 | Mahfouz | ................. | G16H 50/30 |
| | | | | 600/443 |
| 2014/0221836 A1* | 8/2014 | Takeda | .................... | A61B 8/463 |
| | | | | 600/443 |
| 2014/0275954 A1* | 9/2014 | Ohta | ........................ | A61B 8/465 |
| | | | | 600/407 |
| 2015/0164479 A1* | 6/2015 | Toji | .......................... | A61B 8/463 |
| | | | | 600/440 |
| 2015/0182191 A1* | 7/2015 | Caluser | ................. | A61B 8/5246 |
| | | | | 600/407 |
| 2015/0209015 A1* | 7/2015 | Oh | ........................... | A61B 8/463 |
| | | | | 600/443 |
| 2015/0327841 A1* | 11/2015 | Banjanin | .............. | A61B 8/4263 |
| | | | | 600/443 |
| 2015/0342563 A1* | 12/2015 | Takahashi | .............. | A61B 8/465 |
| | | | | 600/440 |
| 2017/0215842 A1* | 8/2017 | Ryu | ...................... | A61B 8/4245 |
| 2017/0252002 A1* | 9/2017 | Mine | .................... | A61B 8/4218 |
| 2019/0038260 A1* | 2/2019 | Lee | ......................... | A61B 8/582 |
| 2019/0200955 A1* | 7/2019 | Ryu | ........................ | A61B 8/463 |
| 2021/0065365 A1* | 3/2021 | Odagiri | .................... | G06T 7/70 |
| 2021/0128265 A1* | 5/2021 | Jin | ......................... | A61B 8/4472 |
| 2022/0387000 A1* | 12/2022 | Yoo | ....................... | A61B 8/4254 |
| 2023/0103969 A1* | 4/2023 | St. Pierre | .............. | G06T 7/0014 |
| | | | | 382/128 |

FOREIGN PATENT DOCUMENTS

| | | | | |
|---|---|---|---|---|
| JP | 2015-226607 A | 12/2015 | | |
| JP | 2019-193778 A | 11/2019 | | |
| JP | 2021-029676 A | 3/2021 | | |
| JP | 6850896 B2 * | 3/2021 | ............... | A61B 8/54 |

OTHER PUBLICATIONS

International Search Report issued in PCT/JP2022/010475; mailed May 31, 2022.

International Preliminary Report on Patentability (Chapter I) and Written Opinion of the International Searching Authority issued in PCT/JP2022/010475; issued Sep. 12, 2023.

An Office Action; "Notice of Reasons for Refusal," mailed by the Japanese Patent Office on Oct. 7, 2025, which corresponds to Japanese Patent Application No. 2023-508979 and is related to U.S. Appl. No. 18/467,926; with English language translation.

* cited by examiner

TRANSDUCER ARRAY —11

TRANSMISSION AND RECEPTION CIRCUIT —13

PULSAR —51

AMPLIFICATION SECTION —53

AD CONVERSION SECTION —55

BEAM FORMER —57

ULTRASOUND IMAGE GENERATION UNIT —31

SIGNAL PROCESSING SECTION —21

DSC —23

IMAGE PROCESSING SECTION —25

41
61
63
65
67

41
61
63

73 — ULTRASOUND IMAGE — 71

75 — CAMERA IMAGE  STORE — 77

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

This application is a Continuation of PCT International Application No. PCT/JP2022/010475 filed on Mar. 10, 2022, which claims priority under 35 U.S.C. § 119(a) to Japanese Patent Application No. 2021-047388 filed on Mar. 22, 2021. The above applications are hereby expressly incorporated by reference, in their entirety, into the present application.

BACKGROUND OF THE INVENTION

1. Field of the Invention

The present invention relates to an ultrasound diagnostic apparatus and a control method for an ultrasound diagnostic apparatus for generating an ultrasound image including an examination area of a subject under examination.

2. Description of the Related Art

In a case where an examination of a subject under examination is performed using an ultrasound diagnostic apparatus, it is important to record, for example, an ultrasound image including an examination area, and a body mark for specifying a position and an orientation of an ultrasound probe at the time of generating the ultrasound image in association with each other, for the use in subsequent diagnosis.

Conventionally, adding the body mark to the ultrasound image has been very laborious and time-consuming because it is necessary to manually add a probe mark representing the position and the orientation of the ultrasound probe at the time of generating the ultrasound image to the body mark to be added to the ultrasound image for each ultrasound image.

In response to this, JP2015-131099A, JP2019-193778A, or the like has proposed that an ultrasound image and an optical image (video image) of a subject under examination at the time of generating the ultrasound image are stored in association with each other.

SUMMARY OF THE INVENTION

In JP2015-131099A and JP2019-193778A, the optical image can be referred to instead of the body mark. However, as in JP2015-131099A and JP2019-193778A, simply associating and storing the ultrasound image and the optical image may pose a problem that, for example, in subsequent diagnosis, it takes time and effort to reselect a desired single frame of the ultrasound image and a desired single frame of the optical image from among the associated and stored ultrasound images and optical images each time the images at the time of the examination are viewed again.

An object of the present invention is to provide an ultrasound diagnostic apparatus and a control method for an ultrasound diagnostic apparatus capable of eliminating the time and effort required to reselect a desired image in a case where an optical image is used instead of a body mark.

In order to achieve the above-described object, according to the present invention, there is provided an ultrasound diagnostic apparatus comprising:

an ultrasound probe; and an apparatus main body connected to the ultrasound probe, in which the apparatus main body includes an ultrasound image generation unit configured to generate an ultrasound image including an examination area of a subject under examination from a reception signal obtained by transmitting and receiving an ultrasound beam to and from the examination area using the ultrasound probe, an optical camera configured to generate an optical image including the subject under examination in a state in which the ultrasound probe is in contact, a monitor, a display control unit configured to display the ultrasound image and the optical image on the monitor, a first image memory configured to store the ultrasound image and the optical image generated in a certain period in a past from a timing designated by a user, an image selection unit configured to select a single frame of the ultrasound image and a single frame of the optical image from among the ultrasound images and the optical images stored in the first image memory, and a second image memory configured to store the single frame of the ultrasound image and the single frame of the optical image in association with each other.

Here, it is preferable that the display control unit is configured to display a past ultrasound image designated by the user on the monitor by scrolling back through the ultrasound images stored in the first image memory, and to display a past optical image designated by the user on the monitor by scrolling back through the optical images stored in the first image memory, in response to an instruction from the user.

In addition, it is preferable that the image selection unit is configured to select each of the single frame of the ultrasound image and the single frame of the optical image based on a designation by the user.

Further, it is preferable that the image selection unit is configured to automatically select at least one of the single frame of the ultrasound image or the single frame of the optical image.

Further, it is preferable that the image selection unit is configured to automatically select both the single frame of the ultrasound image and the single frame of the optical image.

Further, it is preferable that the image selection unit is configured to automatically select one image of the single frame of the ultrasound image or the single frame of the optical image, and to automatically select the other image of the single frame of the ultrasound image or the single frame of the optical image from among ultrasound images and optical images generated within a certain period before and after a generation time of the one image among the ultrasound images and the optical images stored in the first image memory.

Further, it is preferable that the image selection unit is configured to select one image of the single frame of the ultrasound image or the single frame of the optical image based on a designation by the user, and to automatically select the other image of the single frame of the ultrasound image or the single frame of the optical image.

Further, it is preferable that the image selection unit is configured to automatically select the other image from among ultrasound images and optical images generated within a certain period before and after a generation time of the one image among the ultrasound images and the optical images stored in the first image memory.

Further, it is preferable that the second image memory is configured to, in a case where processing is performed on at least one of the single frame of the ultrasound image or the single frame of the optical image by the user, store the single frame of the ultrasound image and the single frame of the optical image after the processing in association with each other.

In addition, according to the present invention, there is provided a control method for an ultrasound diagnostic apparatus including an ultrasound probe and an apparatus main body connected to the ultrasound probe, the control method comprising:

a step of generating, via an ultrasound image generation unit provided in the apparatus main body, an ultrasound image including an examination area of a subject under examination from a reception signal obtained by transmitting and receiving an ultrasound beam to and from the examination area using the ultrasound probe;

a step of generating, via an optical camera provided in the apparatus main body, an optical image including the subject under examination in a state in which the ultrasound probe is in contact;

a step of displaying, via a display control unit provided in the apparatus main body, the ultrasound image and the optical image on a monitor provided in the apparatus main body;

a step of storing, via a first image memory provided in the apparatus main body, the ultrasound image and the optical image generated in a certain period in a past from a timing designated by a user;

a step of selecting, via an image selection unit provided in the apparatus main body, a single frame of the ultrasound image and a single frame of the optical image from among the ultrasound images and the optical images stored in the first image memory; and a step of storing, via a second image memory provided in the apparatus main body, the single frame of the ultrasound image and the single frame of the optical image in association with each other.

In the present invention, a single frame of the ultrasound image and a single frame of the optical image are associated and stored. As a result, according to the present invention, for example, in a case where the images at the time of the examination are viewed again by the user in the subsequent diagnosis, it is possible to eliminate the time and effort required to reselect the desired single frame of the ultrasound image and the desired single frame of the optical image from among the ultrasound images and the optical images stored in the first image memory. In addition, the user can easily grasp a position and an orientation of an ultrasound probe 1 at the time of generating the single frame of the ultrasound image associated with the single frame of the optical image by referring to the single frame of the optical image.

DESCRIPTION OF THE PREFERRED EMBODIMENTS

Hereinafter, an ultrasound diagnostic apparatus and a control method for an ultrasound diagnostic apparatus of the embodiment of the present invention will be described in detail based on suitable embodiments shown in the accompanying drawings.

Figure 1:
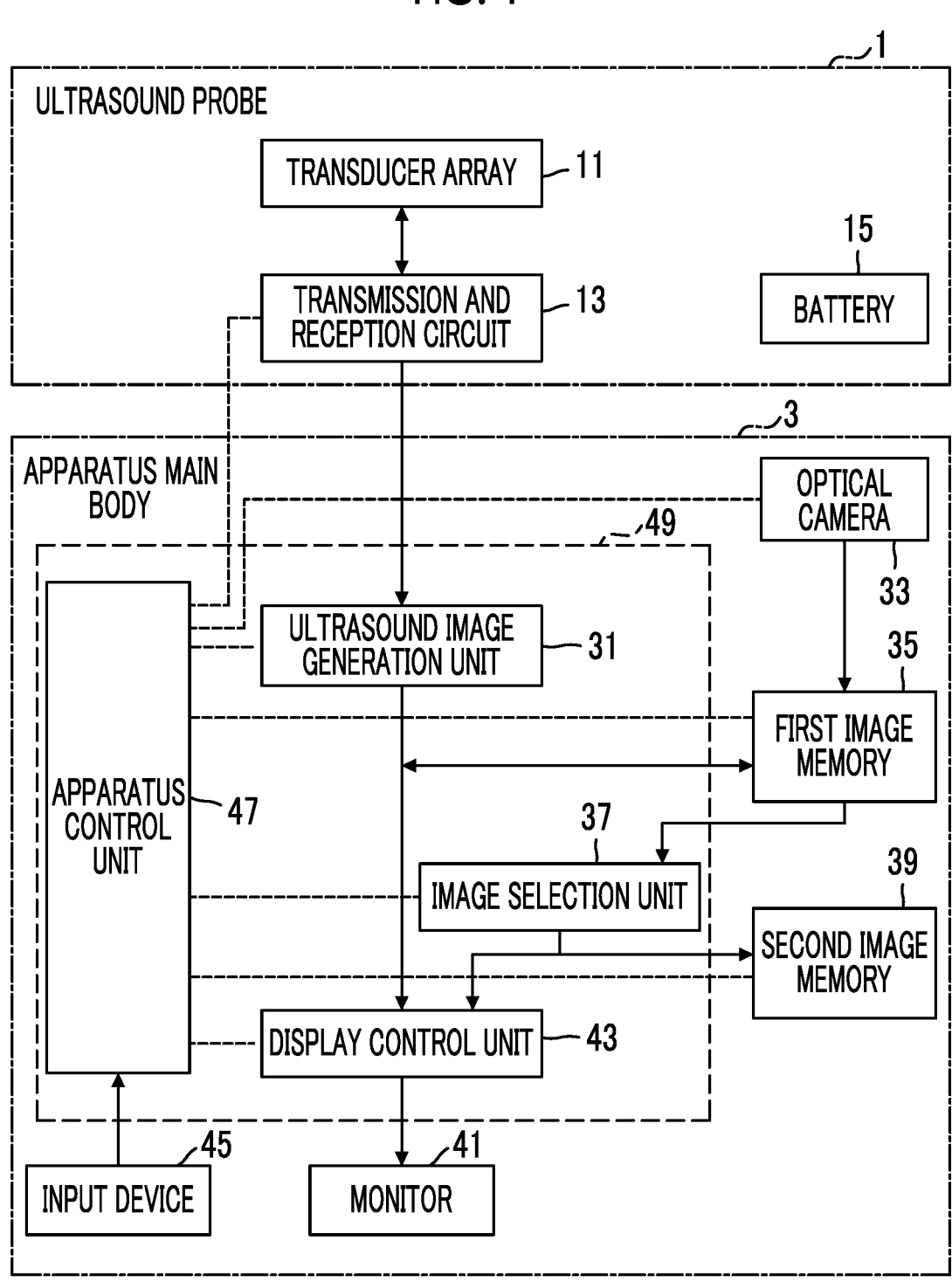
FIG. 1 is a block diagram of one embodiment showing a configuration of an ultrasound diagnostic apparatus.

FIG. 1 is a block diagram of one embodiment showing a configuration of the ultrasound diagnostic apparatus of the embodiment of the present invention. The ultrasound diagnostic apparatus shown in FIG. 1 is a handheld ultrasound diagnostic apparatus and comprises an ultrasound probe 1 and an apparatus main body 3 connected to the ultrasound probe 1. The ultrasound diagnostic apparatus of the present embodiment is realized by the ultrasound probe 1, the apparatus main body 3, and an application program for ultrasound diagnosis that operates on the apparatus main body 3.

The ultrasound probe 1 scans an examination area of a subject under examination with an ultrasound beam and outputs a sound ray signal corresponding to an ultrasound image of the examination area. As shown in FIG. 1, the ultrasound probe 1 comprises a transducer array 11, a transmission and reception circuit 13, and a battery 15. The transducer array 11 and the transmission and reception circuit 13 are bidirectionally connected, and an apparatus control unit 47 of the apparatus main body 3, which will be described below, is connected to the transmission and reception circuit 13. In addition, the ultrasound probe 1 incorporates the battery 15.

The transducer array 11 includes a plurality of ultrasound transducers arranged one-dimensionally or two-dimensionally. Each of these transducers transmits an ultrasound wave in accordance with a drive signal supplied from the transmission and reception circuit 13 and outputs an analog reception signal by receiving a reflected wave from the subject under examination.

For example, each transducer is composed of an element obtained by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figures 2, 3:
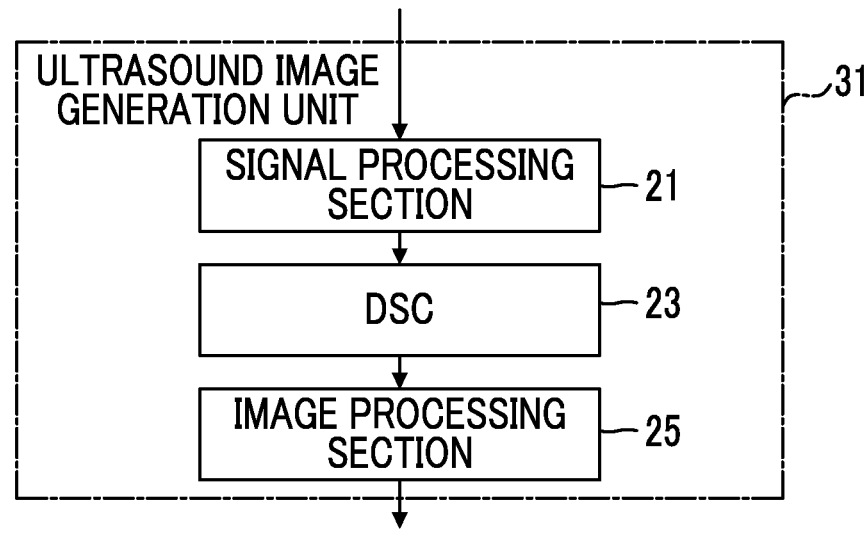
FIG. 2 is a block diagram of one embodiment showing a configuration of a transmission and reception circuit.
FIG. 3 is a block diagram of one embodiment showing a configuration of an ultrasound image generation unit.

Under the control of the apparatus control unit 47, the transmission and reception circuit 13 generates the sound ray signal by transmitting an ultrasound beam from the transducer array 11 and performing reception focus processing on a reception signal output from the transducer array 11, which has received an ultrasound echo. As shown in FIG. 2, the transmission and reception circuit 13 includes a pulsar 51 connected to the transducer array 11, an amplification section 53, an analog-to-digital (AD) conversion section 55, and a beam former 57 that are sequentially connected in series to the transducer array 11.

The pulsar 51 includes, for example, a plurality of pulse generators, and performs transmission focus processing of supplying respective drive signals to the plurality of trans- ducers by adjusting amounts of delay such that ultrasound waves transmitted from the plurality of transducers of the transducer array 11 form an ultrasound beam, based on a transmission delay pattern selected by the apparatus control unit 47. In a case where a pulsed or continuous-wave voltage is applied to the electrodes of the transducer of the trans- ducer array 11 through the transmission focus processing, the piezoelectric body expands and contracts, and a pulsed or continuous-wave ultrasound wave is generated from each of the transducers, whereby the ultrasound beam is formed from a combined wave of these ultrasound waves.

The transmitted ultrasound beam is reflected in, for example, a target such as a site of the subject under exami- nation and propagates toward the transducer array 11 of the ultrasound probe 1. Each of the transducers constituting the transducer array 11 expands and contracts by receiving the ultrasound echo propagating toward the transducer array 11 in this manner, generates a reception signal, which is an electrical signal, and outputs the reception signals to the amplification section 53.

The amplification section 53 amplifies the signal input from each of the transducers constituting the transducer array 11 and transmits the amplified signal to the AD conversion section 55. The AD conversion section 55 con- verts the analog signal transmitted from the amplification section 53 into digital reception data and outputs the recep- tion data to the beam former 57.

The beam former 57 performs so-called reception focus processing of performing addition by applying a delay to each reception data converted by the AD conversion section 55 in accordance with a sound velocity or a sound velocity distribution set based on a reception delay pattern selected by the apparatus control unit 47. By this reception focus processing, each reception data converted by the AD con- version section 55 is phase-added, and a sound ray signal in which the focus of the ultrasound echo is narrowed down is generated.

The battery 15 is incorporated into the ultrasound probe 1 and supplies power to each circuit of the ultrasound probe 1.

Next, the apparatus main body 3 generates an ultrasound image including the examination area of the subject under examination based on the sound ray signal generated by the ultrasound probe 1 and displays the ultrasound image including the examination area of the subject under exami- nation. The apparatus main body 3 is, for example, a handheld terminal apparatus, such as a smartphone or a tablet personal computer (PC), and comprises an ultrasound image generation unit 31, an optical camera 33, a first image memory 35, an image selection unit 37, a second image memory 39, a monitor 41, a display control unit 43, an input device 45, and the apparatus control unit 47, as shown in FIG. 1.

The ultrasound image generation unit 31 is connected to the transmission and reception circuit 13 of the ultrasound probe 1, and the display control unit 43 and the monitor 41 are sequentially connected to the ultrasound image genera- tion unit 31. In addition, the first image memory 35 is connected to each of the ultrasound image generation unit 31 and the display control unit 43. Further, the first image memory 35 and the image selection unit 37 are sequentially connected to the optical camera 33, and the second image memory 39 and the display control unit 43 are each connected to the image selection unit 37. The apparatus control unit 47 is connected to the transmission and reception circuit 13, the ultrasound image generation unit 31, the optical camera 33, the display control unit 43, the first image memory 35, the image selection unit 37, and the second image memory 39, and the apparatus control unit 47 is connected to the input device 45.

The ultrasound probe 1 and the apparatus main body 3 are connected via wireless connection using wireless commu- nication, such as wireless fidelity (Wi-Fi), or connected via wired connection using a cable, such as a universal serial bus (USB) cable.

Under the control of the apparatus control unit 47, the ultrasound image generation unit 31 generates the ultra- sound image (ultrasound image signal) including the exami- nation area of the subject under examination from the reception signal obtained by transmitting and receiving the ultrasound beam to and from the examination area of the subject under examination using the ultrasound probe 1 (more precisely, the transducer array 11), more specifically, from the sound ray signal generated from the reception signal by the transmission and reception circuit 13. As shown in FIG. 3, the ultrasound image generation unit 31 has a configuration in which a signal processing section 21, a DSC 23, and an image processing section 25 are sequentially connected in series.

The signal processing section 21 generates image infor- mation data corresponding to the ultrasound image based on the sound ray signal generated by the transmission and reception circuit 13. More specifically, the signal processing section 21 performs signal processing on the sound ray signal generated by the beam former 57 of the transmission and reception circuit 13, for example, corrects the attenua- tion caused by a propagation distance according to the depth of a position where the ultrasound wave is reflected, and then performs envelope detection processing to generate the image information data representing tomographic image information regarding tissues inside the subject under examination.

The digital scan converter (DSC) 23 raster-converts the image information data generated by the signal processing section 21 into an image signal according to a scanning method of a normal television signal.

The image processing section 25 performs various types of image processing such as brightness correction, gradation correction, sharpness correction, image size correction, refresh rate correction, scanning frequency correction, and color correction according to a display format of the monitor 41 on the image signal input from the DSC 23 to generate the ultrasound image, and outputs the ultrasound image, which has been subjected to the image processing, to the first image memory 35 and the display control unit 43.

Under the control of the apparatus control unit 47, the optical camera 33 generates an optical image (camera image) including the subject under examination in a state in which the ultrasound probe 1 is in contact by imaging the subject under examination during the examination of the examination area using the ultrasound probe 1.

Under the control of the apparatus control unit 47, the first image memory 35 stores a series of a plurality of frames of ultrasound images (video images) generated by the ultra- sound image generation unit 31 and a series of a plurality of frames of optical images (video images) generated by the optical camera 33 for each examination.

In the first image memory 35, the ultrasound images (still images) and the optical images (still images) are sequen- tially stored independently of each other until the storage capacity of the first image memory 35 becomes full. It is not necessary to match generation times (time stamps) of the ultrasound image and the optical image at the time of storage. In other words, it is not necessary to store frames of the ultrasound image and the optical image with the same generation time as a set. After that, in the first image memory 35, latest frames of the ultrasound image and the optical image are sequentially overwritten onto oldest frames of the ultrasound image and the optical image, respectively. As a result, the first image memory 35 stores an ultrasound image and an optical image generated in a certain period in the past from the latest frames of the ultrasound image and the optical image.

Under the control of the apparatus control unit 47, the image selection unit 37 selects a single frame of the ultrasound image and a single frame of the optical image from among the ultrasound images and the optical images stored in the first image memory 35.

Details of a method of selecting a single frame of the ultrasound image and a single frame of the optical image will be described below.

Under the control of the apparatus control unit 47, the second image memory 39 stores the single frame of the ultrasound image and the single frame of the optical image, which are selected by the image selection unit 37, in association with each other.

The display control unit 43 displays various types of information on the monitor (display unit) 41 under the control of the apparatus control unit 47. The monitor 41 displays, for example, an operation screen for selecting the single frame of the ultrasound image and the single frame of the optical image, and the like, in addition to the ultrasound image and the optical image. The monitor 41 is not particularly limited, but examples thereof include a liquid crystal display (LCD) and an organic electro-luminescence (EL) display.

The monitor 41 is disposed on one surface of the apparatus main body 3. On the other hand, the optical camera 33 is disposed on the other surface of the apparatus main body 3, that is, on a surface opposite to the surface on which the monitor 41 is disposed.

The input device 45 receives various instructions input from a user (examiner) of the ultrasound diagnostic apparatus. The input device 45 is not particularly limited, but includes, for example, various buttons, a touch panel on which the user performs a touch operation to input various instructions, and the like.

The apparatus control unit 47 controls each unit of the ultrasound probe 1 and the apparatus main body 3 based on a program stored in advance and an instruction or the like of the user input through the input device 45.

The ultrasound image generation unit 31, the image selection unit 37, the display control unit 43, and the apparatus control unit 47 are configured by a processor 49.

Figure 4:
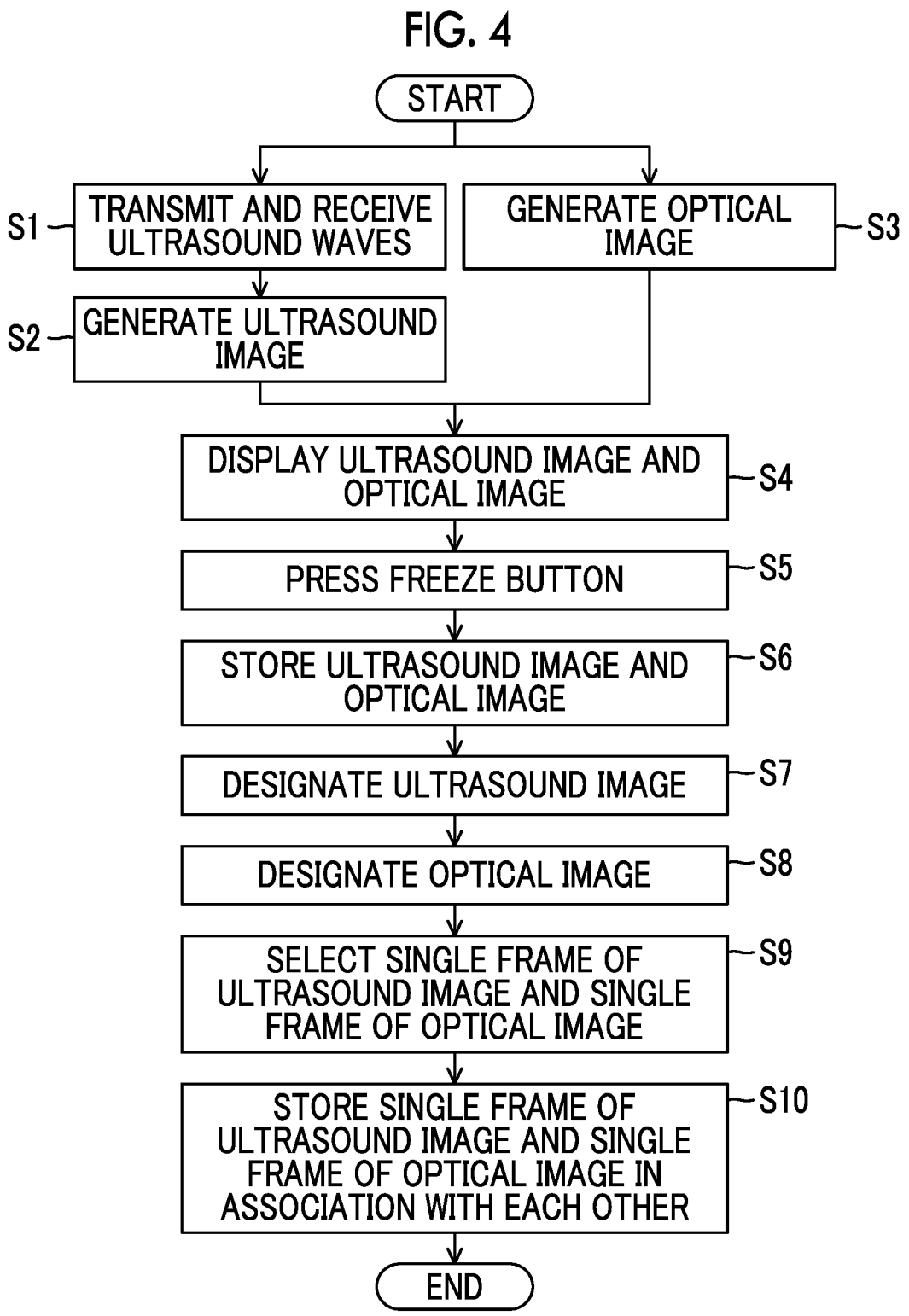
FIG. 4 is a flowchart of one embodiment showing an operation of the ultrasound diagnostic apparatus.

Next, the operation of the ultrasound diagnostic apparatus will be described with reference to the flowchart of FIG. 4.

In a case of examining the subject under examination, the user first brings the ultrasound probe 1 into contact with the examination area of the subject under examination to start transmission and reception of ultrasound waves and uses the optical camera 33 to image the subject under examination including the ultrasound probe 1 during the examination of the examination area.

In this case, under the control of the apparatus control unit 47, the transmission and reception circuit 13 performs the transmission and reception of ultrasound waves in a state in which the ultrasound probe 1 is in contact with the examination area of the subject under examination, thereby generating the sound ray signal (step S1).

That is, the ultrasound beam is transmitted to the examination area of the subject under examination from the plurality of transducers of the transducer array 11 in accordance with the drive signal from the pulsar 51.

The ultrasound echo from the examination area based on the ultrasound beam transmitted from the pulsar 51 is received by each transducer of the transducer array 11, and the reception signal, which is an analog signal, is output from each transducer of the transducer array 11 that has received the ultrasound echo.

The reception signal output from each transducer of the transducer array 11 is amplified by the amplification section 53 and is subjected to AD conversion by the AD conversion section 55, whereby the reception data is acquired.

The sound ray signal is generated by performing the reception focus processing on the reception data through the beam former 57.

Subsequently, under the control of the apparatus control unit 47, the ultrasound image generation unit 31 generates the ultrasound image including the examination area of the subject under examination based on the sound ray signal generated by the beam former 57 of the transmission and reception circuit 13 (step S2).

That is, the sound ray signal generated by the beam former 57 is subjected to various types of signal processing by the signal processing section 21, and the image information data representing tomographic image information regarding tissues inside the subject under examination is generated.

The image information data generated by the signal processing section 21 is raster-converted by the DSC 23 and is further subjected to various types of image processing by the image processing section 25, whereby the ultrasound images (video images) are sequentially generated.

Meanwhile, under the control of the apparatus control unit 47, the optical camera 33 uses the ultrasound probe 1 to image the subject under examination during the examination of the examination area, thereby sequentially generating the optical images (video images) including the subject under examination in a state in which the ultrasound probe 1 is in contact (step S3).

That is, the ultrasound image in which the examination area of the subject under examination is captured and the optical image in which the subject under examination including the ultrasound probe 1 during the examination of the examination area is captured are generated at the same time.

The ultrasound image generated by the ultrasound image generation unit 31 and the optical image generated by the optical camera 33 are sequentially stored in the first image memory 35 under the control of the apparatus control unit 47.

Figure 5:
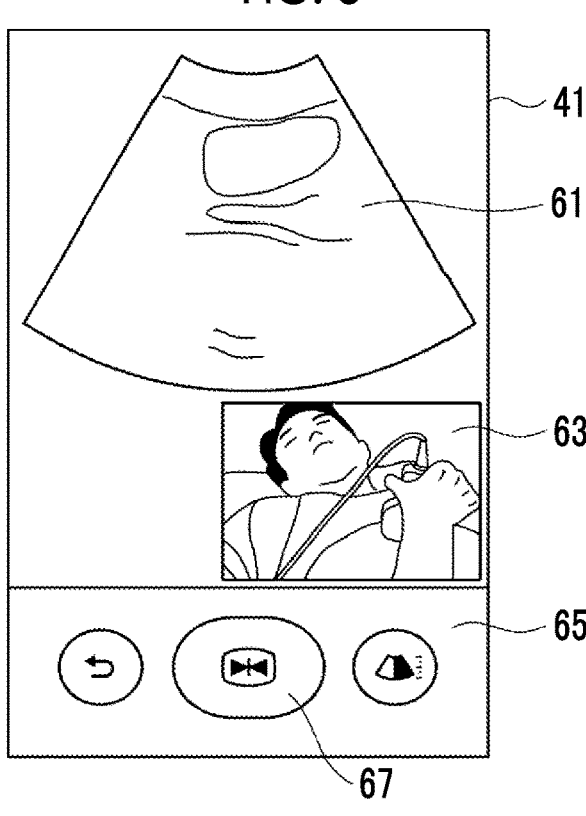
FIG. 5 is a conceptual diagram of one embodiment showing a display screen of a monitor during examination of a subject under examination.

In addition, as shown in FIG. 5, under the control of the apparatus control unit 47, the display control unit 43 sequentially displays the ultrasound image generated by the ultrasound image generation unit 31 and the optical image generated by the optical camera 33 on the monitor 41 (step S4).

Therefore, the user can use the ultrasound probe 1 to generate the ultrasound image including the examination area of the subject under examination while viewing the ultrasound image and the optical image displayed on the display screen of the monitor 41 disposed on one surface of the apparatus main body 3, and at the same time, can use the optical camera 33 disposed on the other surface of the apparatus main body 3 to generate the optical image including the subject under examination in a state in which the ultrasound probe 1 is in contact with the examination area.

FIG. 5 is a conceptual diagram of one embodiment showing the display screen of the monitor during the examination of the subject under examination. An ultrasound image 61 is displayed in a region of an upper part in the display screen of the monitor 41 shown in FIG. 5, and an optical image 63 is displayed in a region below the ultrasound image 61, from a center part to a right end part. A first operation screen 65 is displayed in a region below the optical image 63. A freeze button 67 is disposed in a center part of the first operation screen.

Here, the user presses the freeze button 67, for example, at a timing at which the user considers that a desired ultrasound image including the examination area of the subject under examination is generated, while viewing the ultrasound image and the optical image sequentially displayed on the monitor 41 of the apparatus main body 3 (step S5).

In a case where the freeze button 67 is pressed, the ultrasound image and the optical image generated in a certain period in the past from the timing in which the freeze is designated by the user are stored in the first image memory 35 under the control of the apparatus control unit 47 (step S6). In other words, the ultrasound image and the optical image, which are already stored in the first image memory 35 and are generated in a certain period in the past from the timing in which the freeze is designated by the user, are held in the first image memory 35 as they are.

Figure 6:
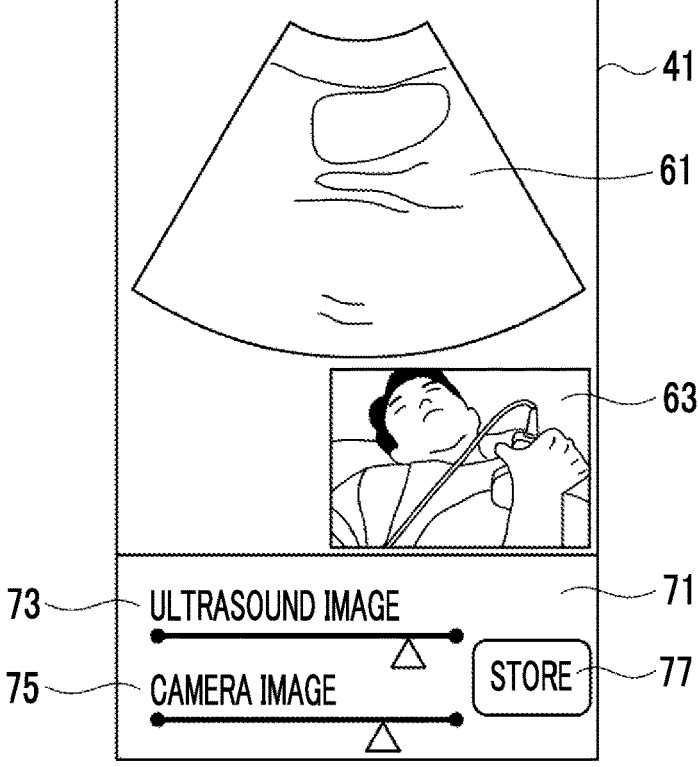
FIG. 6 is a conceptual diagram of another embodiment showing the display screen of the monitor after a freeze button is pressed.

Further, in a case where the freeze button 67 is pressed, the display control unit 43 displays a second operation screen 71 on the monitor 41 as shown in FIG. 6 instead of the first operation screen 65 shown in FIG. 5.

FIG. 6 is a conceptual diagram of another embodiment showing the display screen of the monitor after the freeze button is pressed. FIG. 6 shows a state in which the second operation screen 71 is displayed instead of the first operation screen 65 on the display screen of the monitor 41 shown in FIG. 5. In the second operation screen 71, from a left end part to a center part, a slide bar 73 for an ultrasound image is disposed on an upper side and a slide bar 75 for an optical image (camera image) is disposed on a lower side. In addition, a store button 77 is disposed on a right part of the second operation screen 71.

Subsequently, the user uses the slide bar 73 for an ultrasound image and the slide bar 75 for an optical image to designate the desired single frame of the ultrasound image and the desired single frame of the optical image from among the ultrasound images and the optical images stored in the first image memory 35, respectively.

A left-right direction of the slide bar 73 for an ultrasound image represents a time axis, and a position of a right end thereof corresponds to the generation time of the latest frame of the ultrasound image among the ultrasound images stored in the first image memory 35, and a position of a left end thereof corresponds to the generation time of the oldest frame of the ultrasound image.

The user sequentially moves a knob represented by a triangle from the position of the right end of the slide bar 73 for an ultrasound image to the left side, whereby it is possible to display the past frame of the ultrasound image on the monitor 41 by sequentially scrolling back from the latest frame of the ultrasound image to the past frame of the ultrasound image. In addition, by stopping the movement of the knob, the user can designate the single frame of the ultrasound image corresponding to the generation time of the position where the movement of the knob is stopped from among the ultrasound images stored in the first image memory 35.

The same applies to the operation of the slide bar 75 for an optical image.

That is, in a case where the user moves the knob of the slide bar 73 for an ultrasound image to the left or right, in response to this instruction, the past ultrasound image designated by the user by moving the knob and scrolling back from among the ultrasound images stored in the first image memory 35 is displayed on the monitor 41 by the display control unit 43. In addition, in a case where the user stops the movement of the knob at a desired position, the single frame of the ultrasound image corresponding to the generation time of the position where the movement of the knob is stopped is designated (step S7).

In addition, in a case where the user moves the knob of the slide bar 75 for an optical image to the left or right, in response to this instruction, the past optical image designated by the user by moving the knob and scrolling back from among the optical images stored in the first image memory 35 is displayed on the monitor 41 by the display control unit 43. In addition, in a case where the user stops the movement of the knob at a desired position, the single frame of the optical image corresponding to the generation time of the position where the movement of the knob is stopped is designated (step S8).

The user presses the store button 77 after designating each of the desired single frame of the ultrasound image and the desired single frame of the optical image.

In response to this, under the control of the apparatus control unit 47, the image selection unit 37 selects each of the single frame of the ultrasound image and the single frame of the optical image from among the ultrasound images and the optical images stored in the first image memory 35 based on the designation by the user (step S9).

Subsequently, under the control of the apparatus control unit 47, the single frame of the ultrasound image and the single frame of the optical image selected by the image selection unit 37 are associated and stored in the second image memory 39 (step S10).

In the ultrasound diagnostic apparatus of the present embodiment, the single frame of the ultrasound image and the single frame of the optical image are associated and stored. As a result, for example, in a case where the images at the time of the examination are viewed again by the user in the subsequent diagnosis, it is possible to eliminate the time and effort required to reselect the desired single frame of the ultrasound image and the desired single frame of the optical image from among the ultrasound images and the optical images stored in the first image memory 35. In addition, the user can easily grasp a position and an orientation of an ultrasound probe 1 at the time of generating the single frame of the ultrasound image associated with the single frame of the optical image by referring to the single frame of the optical image.

The user can perform various types of processing on at least one of the single frame of the ultrasound image or the single frame of the optical image designated by the user.

In this case, the user can perform various types of processing on the ultrasound image 61 by, for example, pressing the ultrasound image 61 on the display screen shown in FIG. 6 to enter a processing mode of the ultrasound image.

In the processing mode, for example, the user can add an annotation comment (annotation) related to the ultrasound image to the ultrasound image 61 or perform various types of image processing including sharpening of the image and the like. The same applies to the optical image, and the user can perform various types of processing on the optical image by pressing the optical image 63 to enter a processing mode of the optical image.

In this way, in a case where processing is performed on at least one of the single frame of the ultrasound image or the single frame of the optical image by the user, the single frame of the ultrasound image and the single frame of the optical image after the processing are associated and stored in the second image memory 39.

In addition, the image selection unit 37 can not only select the single frame of the ultrasound image and the single frame of the optical image designated by the user, but also can automatically select at least one of the single frame of the ultrasound image or the single frame of the optical image.

For example, the image selection unit 37 may automatically select both the single frame of the ultrasound image and the single frame of the optical image in a case where the freeze button 67 is pressed.

The method of automatically selecting the ultrasound image is not particularly limited as long as it is possible to automatically select the ultrasound image in which the examination area of the subject under examination is shown, more specifically, the ultrasound image in which the examination area is most clearly shown. For example, in a case where the examination area is designated in advance by the user, the image selection unit 37 can automatically select the single frame of the ultrasound image including the examination area by identifying the examination area included in the ultrasound image through image recognition processing for each ultrasound image stored in the first image memory 35.

The image selection unit 37 can use, for example, a determination model by machine learning as the image recognition processing of identifying the examination area included in the ultrasound image.

The determination model is a trained model that has learned, using a learning ultrasound image including the same examination area of any subject under examination as training data, a relationship between the learning ultrasound image and the examination area included in this learning ultrasound image for a plurality of pieces of the training data.

The determination model outputs, in response to input of an ultrasound image as a determination target, a result of determination (prediction result) of the examination area included in this ultrasound image based on the learning result.

The image selection unit 37 selects the single frame of the ultrasound image including the examination area from the ultrasound images based on the result of the determination by the determination model.

In addition, the method of automatically selecting the optical image is not particularly limited as long as it is possible to select the optical image in which the subject under examination is entirely shown such that the position and the orientation of the ultrasound probe 1 at the time of generating the ultrasound image can be specified. For example, the image selection unit 37 can automatically select the single frame of the optical image including the examination area and the ultrasound probe 1 in a state of being in contact with the subject under examination by identifying the ultrasound probe 1 included in the optical image through the image recognition processing for each optical image stored in the first image memory 35.

Figure 7A:
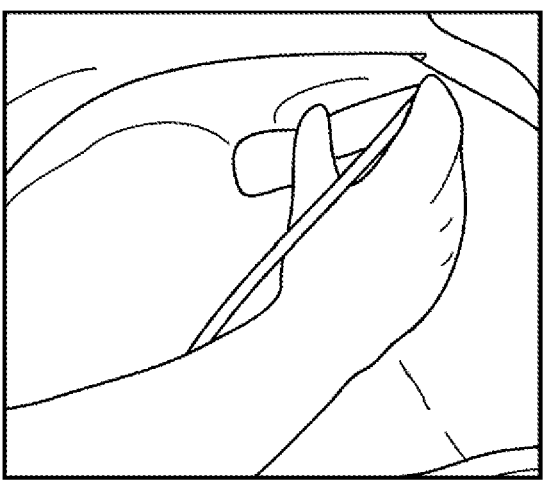
FIG. 7A is a conceptual diagram of one embodiment of an optical image in which the subject under examination whose abdomen is being examined is captured.
Figure 7B:
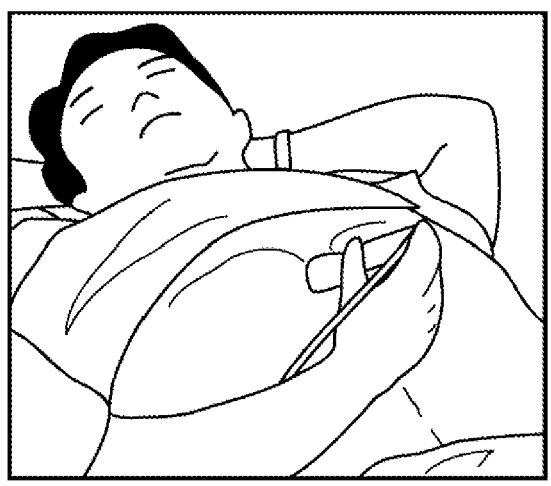
FIG. 7B is a conceptual diagram of another embodiment of the optical image in which the subject under examination whose abdomen is being examined is captured.

For example, FIG. 7A and FIG. 7B are each a conceptual diagram of an optical image in which the subject under examination whose abdomen is being examined is captured.

In the optical image shown in FIG. 7A, the abdomen of the subject under examination including the ultrasound probe is shown larger than the optical image shown in FIG. 7B, but it is difficult to discern that the position with which the ultrasound probe is in contact is the abdomen of the subject under examination because the subject under examination is entirely not shown. On the other hand, in the optical image shown in FIG. 7B, the subject under examination is entirely shown, which makes it possible to clearly discern that the position with which the ultrasound probe is in contact is the abdomen of the subject under examination.

In this case, the image selection unit 37 automatically selects the optical image shown in FIG. 7B, which entirely shows the subject under examination.

The image selection unit 37 can similarly use the determination model by machine learning as the image recognition processing of identifying the ultrasound probe 1 included in the optical image.

By automatically selecting both the single frame of the ultrasound image and the single frame of the optical image, it is possible to eliminate the time and effort required for the user to manually select the image. In a case where the user cannot be satisfied with the automatically selected image, the user may manually reselect the image.

Further, the image selection unit 37 may limit a range in which the single frame of the ultrasound image and the single frame of the optical image are selected from among all the ultrasound images and the optical images stored in the first image memory 35. The generation times (time stamps) of the ultrasound image and the optical image are stored in a case where the images are stored in the first image memory 35. It is possible to limit the range in which the image is selected by using information on the generation time.

In this case, the image selection unit 37 automatically selects one image of the single frame of the ultrasound image or the single frame of the optical image and automatically selects the other image of the single frame of the ultrasound image or the single frame of the optical image from among ultrasound images and optical images generated within a certain period before and after the generation time of the one image among the ultrasound images and the optical images stored in the first image memory 35.

It is not necessary to completely match the generation time of the one image with the generation time of the other image, that is, it is not necessary to select the other image having the same time stamp as that of the one image, and the other image need only be selected from within a certain period before and after the generation time of the one image.

By limiting the range in which the image is selected, it is possible to efficiently select the image in a short time as compared with a case where the single frame of the ultrasound image and the single frame of the optical image are selected from among all the ultrasound images and the optical images stored in the first image memory 35.

It is desirable that the certain period before and after the generation time is, for example, 1 second or more and 2 seconds or less. In a case where the certain period is shorter than 1 second, there is a higher probability that the image may include the influence of camera shake in a case where the user presses the freeze button 67. On the other hand, in a case where the certain period is longer than 2 seconds, for example, there is a higher probability that the image may include an image in which the position other than the examination area is captured because the position of the ultrasound probe 1 is moved.

Alternatively, the image selection unit 37 may select, in a case where one image of the single frame of the ultrasound image or the single frame of the optical image is designated by the user from among the ultrasound images and the optical images stored in the first image memory 35, the one image based on the designation by the user, and automatically select the other image of the single frame of the ultrasound image or the single frame of the optical image.

In this case, the user designates the desired single frame of the ultrasound image by, for example, moving the knob of the slide bar 73 for an ultrasound image to the left or right and then stopping the movement of the knob at a desired position. In response to this, the image selection unit 37 selects the single frame of the ultrasound image manually designated by the user from among the ultrasound images stored in the first image memory 35.

In a case where the single frame of the ultrasound image is designated by the user, the single frame of the optical image is automatically selected from among the optical images stored in the first image memory 35 by the image selection unit 37. In a case where the single frame of the optical image is automatically selected, the knob of the slide bar 75 for an optical image shown in FIG. 6 may be automatically moved to a position corresponding to the generation time of the single frame of the optical image to be automatically selected.

By automatically selecting one image, it is possible to eliminate the time and effort required for the user to manually select the other image. In a case where the user cannot be satisfied with the other image automatically selected, the user may manually reselect the other image.

The one image to be manually designated by the user is not limited to the ultrasound image, and the user may designate the optical image as the one image. However, since the ultrasound image is an image used for diagnosis and the optical image is an image used as a body mark representing the position and the orientation of the ultrasound probe 1 in a case where the ultrasound image is generated, it is desirable that the one image to be manually designated by the user is the ultrasound image.

Similarly, the image selection unit 37 may automatically select the other image from among the ultrasound images and the optical images generated within a certain period before and after the generation time of the one image among the ultrasound images and the optical images stored in the first image memory.

Further, in any of the above-described cases, in a case where one of the single frame of the ultrasound image or the single frame of the optical image is selected, the one image may be first stored in the second image memory 39, and then, in a case where the other image is selected, the other image may be stored in the second image memory 39. Alternatively, after both the single frame of the ultrasound image and the single frame of the optical image are selected, both the images may be stored in the second image memory 39.

As shown in FIG. 1, the apparatus main body 3 may comprise the ultrasound image generation unit 31, but the present invention is not limited to this, and all or only the signal processing section 21 of the ultrasound image generation unit 31 may be provided on an ultrasound probe 1 side.

In the apparatus of the embodiment of the present invention, as the hardware configuration of the processing unit that executes various types of processing, such as the transmission and reception circuit 13, the ultrasound image generation unit 31, the image selection unit 37, the display control unit 43, and the apparatus control unit 47, dedicated hardware may be used, or various processors or computers that execute programs may be used. In addition, as the first image memory 35 and the second image memory 39, recording media, such as a flash memory, a secure digital card (SD card), or a universal serial bus memory (USB memory), may be used, or a hard disk drive (HDD), a solid state drive (SSD), an external server, or the like can also be used.

The various processors include a central processing unit (CPU) which is a general-purpose processor that executes software (programs) to function as various processing units, a programmable logic device (PLD) which is a processor whose circuit configuration is changeable after manufacturing, such as a field programmable gate array (FPGA), and a dedicated electric circuit which is a processor that has a dedicated circuit configuration designed to perform specific processing, such as an application specific integrated circuit (ASIC), and the like.

One processing unit may be composed of one of these various processors or may be composed of a combination of two or more processors of the same type or different types, for example, a combination of a plurality of FPGAs, a combination of an FPGA and a CPU, or the like. In addition, a plurality of processing units may be composed of one of the various processors, or two or more of the plurality of processing units may be collectively composed of one processor.

For example, there is an aspect in which one or more CPUs and software are combined to constitute one processor and the processor functions as a plurality of processing units, as represented by a computer such as a client and a server. In addition, there is an aspect in which a processor that realizes functions of an entire system including a plurality of processing units with one integrated circuit (IC) chip is used, as represented by a system on chip (SoC) or the like.

Further, as the hardware configuration of these various processors, more specifically, an electric circuit (circuitry) in which circuit elements, such as semiconductor elements, are combined is used.

In addition, the method of the embodiment of the present invention can be implemented, for example, by a program for causing a computer to execute each of the steps. Further, it is also possible to provide a computer-readable recording medium on which the program is recorded.

Although the present invention has been described in detail above, the present invention is not limited to the above-described embodiment, and various modifications or changes may be made without departing from the gist of the present invention, of course.

Explanation of References

1: ultrasound probe
3: apparatus main body
11: transducer array
13: transmission and reception circuit
15: battery
21: signal processing section
23: DSC
25: image processing section
31: ultrasound image generation unit
33: optical camera
35: first image memory 37: image selection unit
39: second image memory
41: monitor
43: display control unit
45: input device
47: apparatus control unit
49: processor
51: pulsar
53: amplification section
55: AD conversion section
57: beam former
61: ultrasound image
63: optical image
65: first operation screen
67: freeze button
71: second operation screen
73: slide bar for ultrasound image
75: slide bar for optical image
77: store button

What is claimed is:

1. An ultrasound diagnostic apparatus comprising:
an ultrasound probe; and
an apparatus main body connected to the ultrasound probe,
wherein the apparatus main body includes:
a processor;
a monitor;
an optical camera;
a first image memory; and
a second image memory,
wherein the processor is configured to:
    generate an ultrasound image including an examination area of a subject under examination from a reception signal obtained by transmitting and receiving an ultrasound beam to and from the examination area using the ultrasound probe,
    control the optical camera to generate an optical image including the subject under examination in a state in which the ultrasound probe is in contact,
    display the ultrasound image and the optical image on the monitor,
    sequentially store ultrasound images and optical images independently of each other in the first image memory until a storage capacity of the first image memory becomes full, and then sequentially overwrite latest ultrasound image and latest optical image onto oldest ultrasound image and oldest optical image, respectively, thereby store a plurality of ultrasound images and a plurality of optical images generated up to a timing in which a freeze is designated by a user in the first image memory,
    select a single ultrasound image and a single optical image from among the plurality of ultrasound images and the plurality of optical images stored in the first image memory, and
    store the single ultrasound image and the single optical image in association with each other in the second image memory.

2. The ultrasound diagnostic apparatus according to claim 1,
    wherein the processor is configured to display the single ultrasound image designated by the user on the monitor by scrolling back through the plurality of ultrasound images stored in the first image memory, and to display the single optical image designated by the user on the monitor by scrolling back through the plurality of optical images stored in the first image memory, in response to an instruction from the user.

3. The ultrasound diagnostic apparatus according to claim 2,
    wherein the processor is configured to select each of the single ultrasound image and the single optical image based on the instruction from the user.

4. The ultrasound diagnostic apparatus according to claim 2,
    wherein the processor is configured to select one of the single ultrasound image and the single optical image as a first selected image based on a designation by the user, and to automatically the other of the single ultrasound image and the single optical image as a second selected image.

5. The ultrasound diagnostic apparatus according to claim 4,
    wherein the processor is configured to automatically select the second selected image from among ultrasound images and optical images generated within a predetermined period before and after a generation time of the first selected image among the plurality of ultrasound images and the plurality of optical images stored in the first image memory.

6. The ultrasound diagnostic apparatus according to claim 2,
    wherein the processor is configured to, in a case where processing is performed on at least one of the single ultrasound image or the single optical image by the user, store the single ultrasound image and the single optical image after the processing in association with each other in the second image memory.

7. The ultrasound diagnostic apparatus according to claim 1,
    wherein the processor is configured to select each of the single ultrasound image and the single optical image based on a designation by the user.

8. The ultrasound diagnostic apparatus according to claim 7,
    wherein the processor is configured to, in a case where processing is performed on at least one of the single ultrasound image or the single optical image by the user, store the single ultrasound image and the single optical image after the processing in association with each other in the second image memory.

9. The ultrasound diagnostic apparatus according to claim 1,
    wherein the processor is configured to automatically select either the single ultrasound image or the single optical image.

10. The ultrasound diagnostic apparatus according to claim 9,
    wherein the processor is configured to, in a case where processing is performed on at least one of the single ultrasound image or the single optical image by the user, store the single ultrasound image and the single optical image after the processing in association with each other in the second image memory.

11. The ultrasound diagnostic apparatus according to claim 1,
    wherein the processor is configured to automatically select both the single ultrasound image and the single optical image.

12. The ultrasound diagnostic apparatus according to claim 11,
    wherein the processor is configured to automatically select one of the single ultrasound image and the single optical image as a first selected image, and to automatically select the other of the single ultrasound image and the single optical image as a second selected image from among ultrasound images and optical images generated within a predetermined period before and after a generation time of the first selected image among the plurality of ultrasound images and the plurality of optical images stored in the first image memory.

13. The ultrasound diagnostic apparatus according to claim 11, wherein the processor is configured to, in a case where processing is performed on at least one of the single ultrasound image or the single optical image by the user, store the single ultrasound image and the single optical image after the processing in association with each other in the second image memory.

14. The ultrasound diagnostic apparatus according to claim 1, wherein the processor is configured to select one of the single ultrasound image and the single optical image as a first selected image based on a designation by the user, and to automatically select the other of the single ultrasound image and the single optical image as a second selected image.

15. The ultrasound diagnostic apparatus according to claim 14, wherein the processor is configured to automatically select the second selected image from among ultrasound images and optical images generated within a predetermined period before and after a generation time of the first selected image among the plurality of ultrasound images and the plurality of optical images stored in the first image memory.

16. The ultrasound diagnostic apparatus according to claim 1, wherein the processor is configured to, in a case where processing is performed on at least one of the single ultrasound image or the single optical image by the user, store the single ultrasound image and the single optical image after the processing in association with each other in the second image memory.

17. The ultrasound diagnostic apparatus according to claim 1, wherein the processor is configured to automatically select one of the single ultrasound image and the single optical image as a first selected image, and to automatically select the other of the single ultrasound image and the single optical image as a second selected image from among ultrasound images and optical images generated within a predetermined period before and after a generation time of the first selected image among the plurality of ultrasound images and the plurality of optical images stored in the first image memory.

18. A control method for an ultrasound diagnostic apparatus including an ultrasound probe and an apparatus main body connected to the ultrasound probe, the control method comprising:

generating, via a processor provided in the apparatus main body, an ultrasound image including an examination area of a subject under examination from a reception signal obtained by transmitting and receiving an ultrasound beam to and from the examination area using the ultrasound probe;

controlling an optical camera provided in the apparatus main body to generate, via the processor, an optical image including the subject under examination in a state in which the ultrasound probe is in contact;

displaying, via the processor, the ultrasound image and the optical image on a monitor provided in the apparatus main body;

sequentially storing, via the processor, ultrasound images and optical images independently of each other in a first image memory until a storage capacity of the first image memory becomes full, and then sequentially overwriting, via the processor, latest ultrasound image and latest optical image onto oldest ultrasound image and oldest optical image, respectively, thereby storing, via the processor, a plurality of ultrasound images and a plurality of optical images generated up to a timing in which a freeze is designated by a user in the first image memory provided in the apparatus main body;

selecting, via the processor, a single ultrasound image and a single optical image from among the plurality of ultrasound images and the plurality of optical images stored in the first image memory; and storing, via the processor, the single ultrasound image and the single optical image in association with each other in a second image memory provided in the apparatus main body.

* * * * *